United States Patent
Homan

(10) Patent No.: US 7,922,653 B2
(45) Date of Patent: Apr. 12, 2011

(54) MEDICAL SYSTEM

(75) Inventor: Masatoshi Homan, Hino (JP)

(73) Assignee: Olympus Corporation, Tokyo (JP)

( * ) Notice: Subject to any disclaimer, the term of this patent is extended or adjusted under 35 U.S.C. 154(b) by 1466 days.

(21) Appl. No.: 10/924,345

(22) Filed: Aug. 23, 2004

(65) Prior Publication Data

US 2005/0049488 A1    Mar. 3, 2005

(30) Foreign Application Priority Data

Aug. 29, 2003   (JP) .................................. 2003-307795

(51) Int. Cl.
*A61B 1/00*    (2006.01)
*A61B 1/04*    (2006.01)

(52) U.S. Cl. ....................................................... 600/118

(58) Field of Classification Search .................. 600/101, 600/103, 109, 117–118, 160
See application file for complete search history.

(56) References Cited

U.S. PATENT DOCUMENTS

| | | | | |
|---|---|---|---|---|
| 4,262,632 | A | * | 4/1981 | Hanton et al. ............. 119/51.02 |
| 5,591,217 | A | | 1/1997 | Barreras |
| 6,764,440 | B2 | * | 7/2004 | Iddan et al. .................. 600/109 |
| 7,001,329 | B2 | * | 2/2006 | Kobayashi et al. .......... 600/114 |
| 7,104,952 | B2 | * | 9/2006 | Iddan et al. .................. 600/118 |
| 2001/0035902 | A1 | | 11/2001 | Iddan et al. |
| 2001/0051766 | A1 | * | 12/2001 | Gazdzinski ................... 600/309 |
| 2003/0020810 | A1 | * | 1/2003 | Takizawa et al. ............... 348/68 |
| 2003/0213495 | A1 | * | 11/2003 | Fujita et al. ................... 128/899 |
| 2004/0085441 | A1 | * | 5/2004 | Onishi et al. .................... 348/65 |
| 2004/0092825 | A1 | * | 5/2004 | Madar et al. .................. 600/473 |
| 2004/0111011 | A1 | * | 6/2004 | Uchiyama et al. ............ 600/160 |

FOREIGN PATENT DOCUMENTS

| | | |
|---|---|---|
| EP | 1 277 493 A2 | 1/2003 |
| JP | 57-2014 | 1/1982 |
| JP | 58-019231 | 2/1983 |
| JP | 02-031738 | 2/1990 |
| JP | 2849131 | 11/1998 |
| WO | WO 01/35813 A1 | 5/2001 |

OTHER PUBLICATIONS

Patent Abstracts of Japan Publication No. 02224650, published Sep. 6, 1990.
Abstract of Japanese Patent Publication No. 02-224650, published Sep. 6, 1990.
Japanese Official Action dated Mar. 16, 2010.

* cited by examiner

*Primary Examiner* — Philip R Smith
(74) *Attorney, Agent, or Firm* — Scully, Scott, Murphy & Presser, P.C.

(57) ABSTRACT

A medical system including a capsule type medical device having a capsule configuration, an operation device, arranged external to the capsule type medical device, and including a generator circuit for generating a particular pattern signal, a switch, arranged in the capsule type medical device, for switching on or off power of the capsule type medical device, a receiver, arranged in the capsule type medical device, for receiving a signal from the outside, and a pattern monitoring unit, arranged in the capsule type medical device, for turning on or off the switch at the moment the pattern monitoring unit detects the particular pattern signal as an output signal from the receiver.

15 Claims, 7 Drawing Sheets

FIG.4A ON PATTERN

FIG.4B MAGNETIC FIELD PATTERN

FIG.4C FET 16a

FIG.4D FET 16b

FIG.4E SEMICONDUCTOR SW

FIG.4F MAGNETIC FIELD PATTERN

FIG.4G FET 16a

FIG.4H FET 16b

FIG.4I SEMICONDUCTOR SW

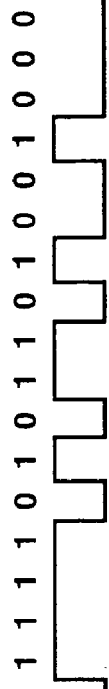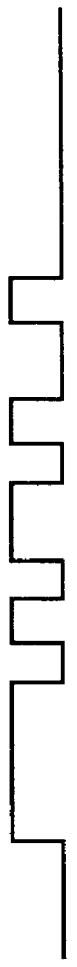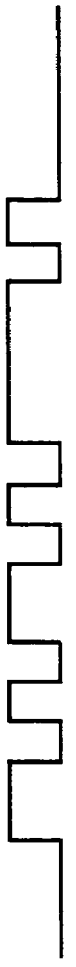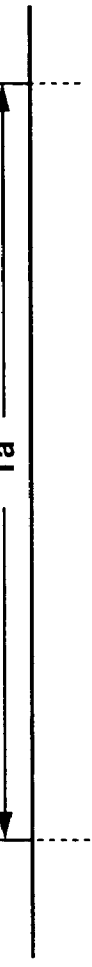
FIG.7A ON PATTERN
FIG.7B MAGNETIC FIELD PATTERN
FIG.7C FET 16a
FIG.7D FET16b
FIG.7E SEMICONDUCTOR SW
FIG.7F MAGNETIC FIELD PATTERN
FIG.7G FET16a
FIG.7H FET16b
FIG.7I SEMICONDUCTOR SW

MEDICAL SYSTEM

CROSS-REFERENCE TO RELATED APPLICATION

This application claims benefits of Japanese Application No. 2003-307795 filed in Japan on Aug. 29, 2003, the contents of which are incorporated by this reference.

BACKGROUND OF THE INVENTION

1. Field of the Invention

The present invention relates to medical systems and, in particular, to a medical system having a capsule type medical device that performs a medical examination and/or a medical treatment in a living body.

2. Description of the Related Art

Capsule type medical devices for performing a medical examination and/or a medical treatment in a living body have been proposed. Patent application PCT WO 01-35813A1 discloses a technique in which a capsule type medical device easy for patients to swallow is used to collect medical images.

In accordance with this technique, the capsule type medical device is housed in a package, and is attached to the package with a magnet prior to use. When the capsule type medical device is used for collecting images, the capsule type medical device is taken out of the package. If the capsule type medical device is removed from the package, the magnetic field of the magnet affects a power supply in the capsule type medical device, thereby causing the power supply to be switched on.

Japanese Patent 2849131 discloses an ultrasonic diagnostic imaging technique in which the power of a capsule type medical device is switched on or off in response to a trigger signal from the outside.

SUMMARY OF THE INVENTION

A medical system of the present invention includes a capsule type medical device having a capsule configuration, an operation device, arranged external to the capsule type medical device, and including a generating circuit for generating a particular pattern signal, a switch, arranged in the capsule type medical device, for switching on and off power of the capsule type medical device, a receiver, arranged in the capsule type medical device, for receiving a signal from the outside, and a pattern monitoring unit, arranged in the capsule type medical device, for turning on or off the switch at the moment the pattern monitoring unit detects a particular pattern signal as an output signal from the receiver.

Additional features and advantages of the invention will be set forth in the description which follows, and in part will be obvious from the description, or may be learned by practice of the invention. The features and advantages of the invention may be realized and obtained by means of the instrumentalities and combinations particularly pointed out hereinafter.

BRIEF DESCRIPTION OF THE DRAWINGS

FIG. 4A is a time chart illustrating the operation of the power switch circuit in the capsule type medical device in accordance with the first embodiment of the present invention;

FIG. 4B is a time chart illustrating the operation of the power switch circuit in the capsule type medical device in accordance with the first embodiment of the present invention;

FIG. 4C is a time chart illustrating the operation of the power switch circuit in the capsule type medical device in accordance with the first embodiment of the present invention;

FIG. 4D is a time chart illustrating the operation of the power switch circuit in the capsule type medical device in accordance with the first embodiment of the present invention;

FIG. 4E is a time chart illustrating the operation of the power switch circuit in the capsule type medical device in accordance with the first embodiment of the present invention;

FIG. 4F is a time chart illustrating the operation of the power switch circuit in the capsule type medical device in accordance with the first embodiment of the present invention;

FIG. 4G is a time chart illustrating the operation of the power switch circuit in the capsule type medical device in accordance with the first embodiment of the present invention;

FIG. 4H is a time chart illustrating the operation of the power switch circuit in the capsule type medical device in accordance with the first embodiment of the present invention;

FIG. 4I is a time chart illustrating the operation of the power switch circuit in the capsule type medical device in accordance with the first embodiment of the present invention;

FIG. 7A is a time chart illustrating the operation of the power switch circuit in the capsule type medical device in accordance with the third embodiment of the present invention;

FIG. 7B is a time chart illustrating the operation of the power switch circuit in the capsule type medical device in accordance with the third embodiment of the present invention;

FIG. 7C is a time chart illustrating the operation of the power switch circuit in the capsule type medical device in accordance with the third embodiment of the present invention;

FIG. 7D is a time chart illustrating the operation of the power switch circuit in the capsule type medical device in accordance with the third embodiment of the present invention;

FIG. 7E is a time chart illustrating the operation of the power switch circuit in the capsule type medical device in accordance with the third embodiment of the present invention;

FIG. 7F is a time chart illustrating the operation of the power switch circuit in the capsule type medical device in accordance with the third embodiment of the present invention;

FIG. 7G is a time chart illustrating the operation of the power switch circuit in the capsule type medical device in accordance with the third embodiment of the present invention;

FIG. 7H is a time chart illustrating the operation of the power switch circuit in the capsule type medical device in accordance with the third embodiment of the present invention; and FIG. 7I is a time chart illustrating the operation of the power switch circuit in the capsule type medical device in accordance with the third embodiment of the present invention.

DETAILED DESCRIPTION OF THE EMBODIMENTS

The embodiments of the present invention will now be discussed with reference to the drawings.

FIGS. 1-3 and FIGS. 4A-4I illustrate a medical system in accordance with a first embodiment of the present invention.

Figure 1:
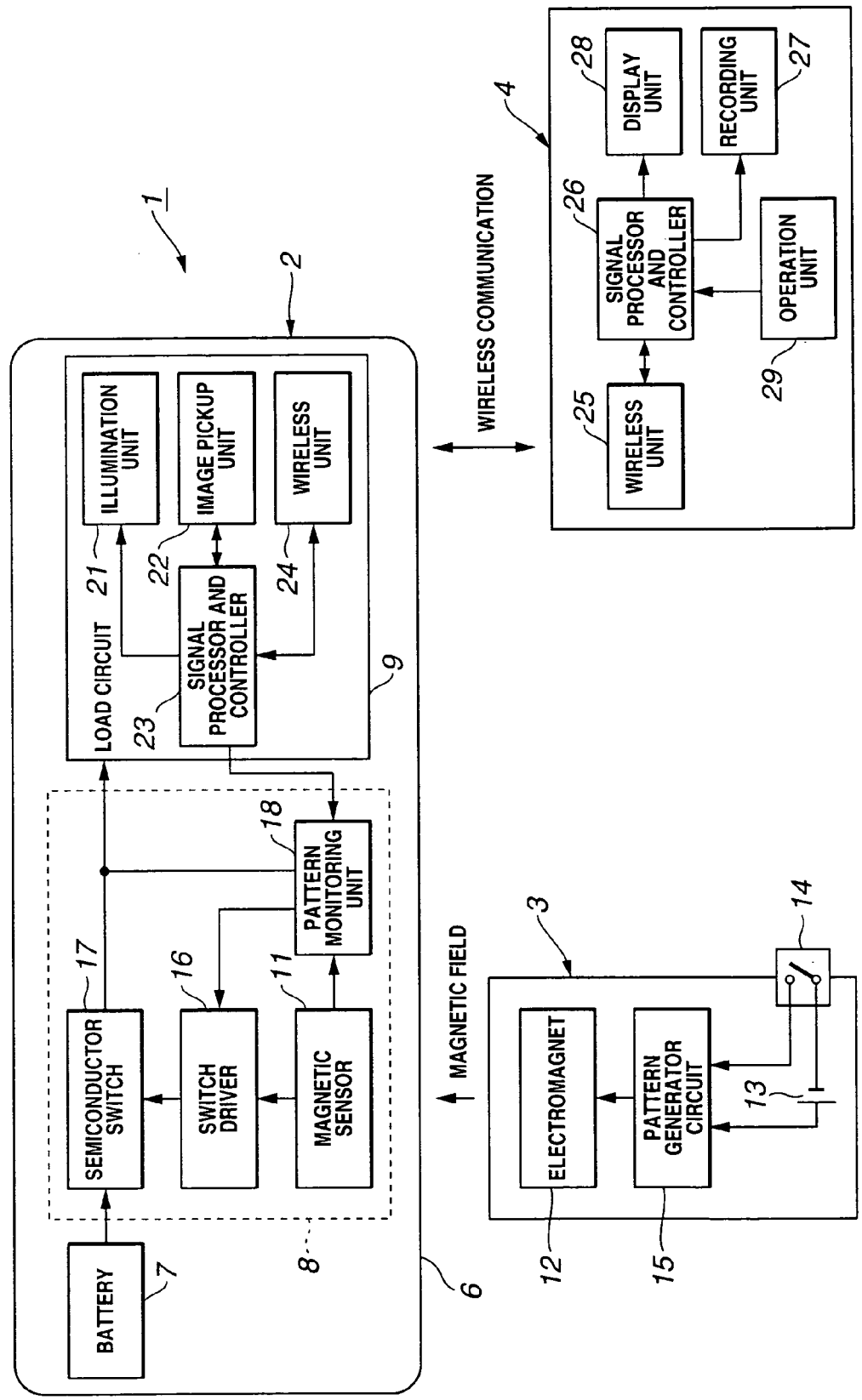
FIG. 1 is a block diagram illustrating the entire structure of a medical system in accordance with a first embodiment of the present invention.

Referring to FIG. 1, the medical system 1 of the first embodiment of the present invention includes a capsule type medical device 2 that collects biomedical information in the body cavity, such as image information when a patient swallows the capsule type medical device 2, a remote controller 3, arranged external to the patient body, for issuing a power on/off command to the capsule type medical device 2, and an external recording device 4 that receives, and records and/or displays the image information acquired from the capsule type medical device 2.

The capsule type medical device 2 in accordance with the first embodiment of the present invention houses a battery 7 within a capsule container 6. The power of the battery 7 is fed to the load circuit 9 through the power switch circuit 8. The power switch circuit 8 switches on or off the power of the battery 7.

The power switch circuit 8 employs a magnetic sensor 11 that detects magnetism (a magnetic field). The remote controller 3 includes an electromagnet 12 that generates a magnetic field to be detected by the magnetic sensor 11.

The remote controller 3 generates a predetermined magnetic pattern signal, thereby causing the power switch circuit 8 to be shifted from an off state to an on state.

A remote controller 3 of FIG. 1 includes a battery 13, a switch 14 for issuing a power on command, a pattern generator circuit 15 for generating a predetermined pattern driving signal in response to the operation of the switch 14, and an electromagnet 12 for generating a magnetism pattern signal corresponding to the pattern driving signal. The pattern driving signal is a digital driving signal of a signal level 0 or 1. The electromagnet 12 generates magnetism in response to the level 1 pattern driving signal while not generating magnetism in response to the level 0 pattern driving signal.

The power switch circuit 8 housed in the capsule type medical device 2 includes the magnetic sensor 11 for detecting the presence or absence of magnetism of the magnetism pattern (binarized magnetism pattern) generated by the electromagnet 12, a switch driver circuit 16 that is set to be operative in response to the presence of magnetism detected by the magnetic sensor 11, a semiconductor switch 17 that is on/off controlled by the switch driver circuit 16, and a pattern monitoring circuit 18 that monitors the magnetism pattern to determine whether or not the magnetism pattern matches a predetermined pattern.

The pattern generator circuit 15 generates a pattern signal in synchronization with a clock signal having a predetermined frequency. The pattern monitoring circuit 18 monitors the magnetism pattern using a clock signal having the same frequency as the pattern generator circuit 15.

As shown in FIG. 1, the load circuit 9 that receives power from the battery 7 through the semiconductor switch 17 includes an illumination unit 21, an image pickup unit 22 for imaging the inside of the body cavity illuminated by the illumination unit 21, a signal processor and controller circuit 23 for driving and controlling the illumination unit 21 and the image pickup unit 22, and for processing an output signal from the image pickup unit 22, and a wireless circuit 24 for wirelessly and outwardly transmitting image information processed signal. These elements are powered from the semiconductor switch 17 in operation.

The external recording device 4 receives the image information wirelessly transmitted by the capsule type medical device 2. The external recording device 4 includes a wireless circuit 25 for receiving a radio wave signal transmitted by the wireless circuit 24 in the capsule type medical device 2 and demodulating the received signal into an image signal, a signal processor and controller circuit 26 for performing image processing on demodulated image information for recording, signal processing for converting the image information into a video signal to be displayed, and control operation, a recording unit 27 for recording the image information, a display unit 28 for displaying the image, and an operation unit 29, such as a keyboard, for sending a control signal to the capsule type medical device 2.

Figure 2:
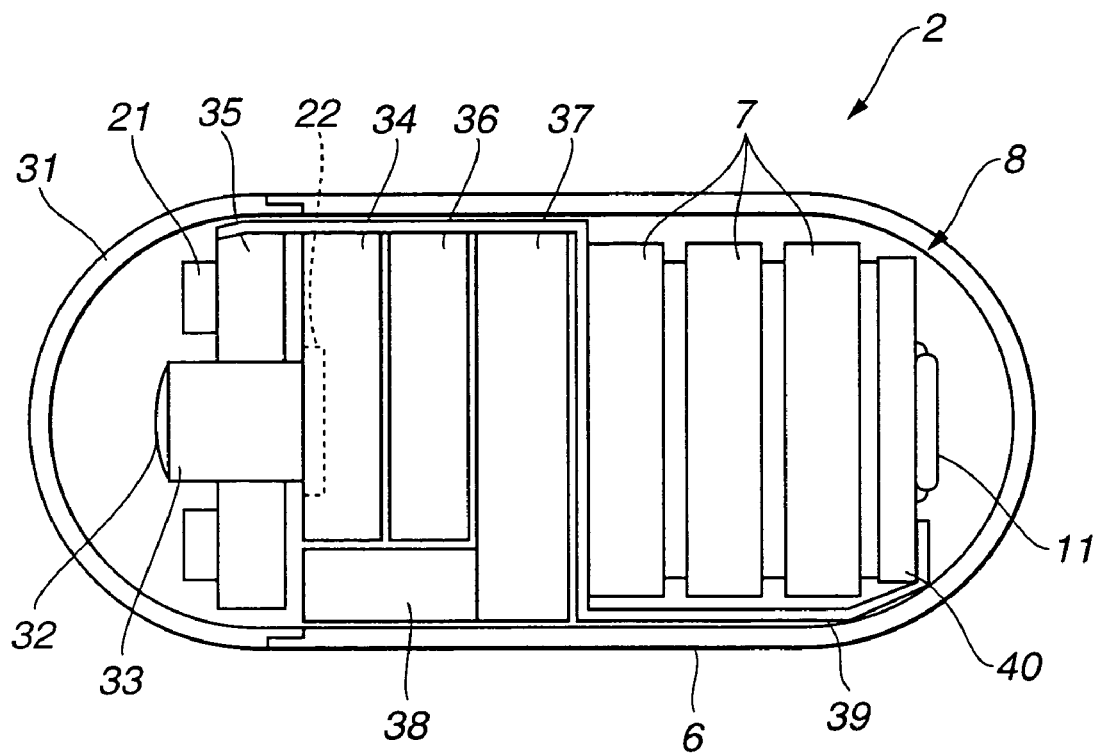
FIG. 2 is a sectional view illustrating the internal structure of a capsule type medical device of the first embodiment.

FIG. 2 illustrates the internal structure of the capsule type medical device 2. The capsule type medical device 2 includes an illumination and image pickup window 31 which is a semi-spherical transparent section at one end of the capsule container 6. The capsule type medical device 2 also includes a lens barrel 33 supporting an objective lens 32 that focuses an image at the focus position. The objective lens 32 is arranged inside of the illumination and image pickup window 31 in the center thereof. An image pickup board 34 is arranged so that an image pickup unit 22 thereof is located at the focus position.

An illumination board 35 having an illumination unit 21 is arranged around the lens barrel 33 to illuminate an imaging area within which the image pickup unit 22 captures images.

A signal processor and controller board 36 bearing the signal processor and controller circuit 26 for performing signal processing and control is arranged next to the image pickup board 34. A wireless board 37 bearing the wireless circuit 24 is arranged adjacent to the signal processor and controller board 36. An antenna 38 is connected to the wireless board 37.

A flexible printed board 39 electrically interconnects the illumination board 35, the image pickup board 34, the signal processor and controller board 36 and the wireless board 37. The flexible printed board 39 is bent on its way to the battery 7 to be connected to the positive electrode of the battery 7. The flexible printed board 39 further extends backward so that the end portion thereof is connected to the power switch circuit 8 which is in turn connected to the negative electrode of the battery 7.

The magnetic sensor 11 is mounted at the center of a switch board 40 bearing the power switch circuit 8.

Figure 3:
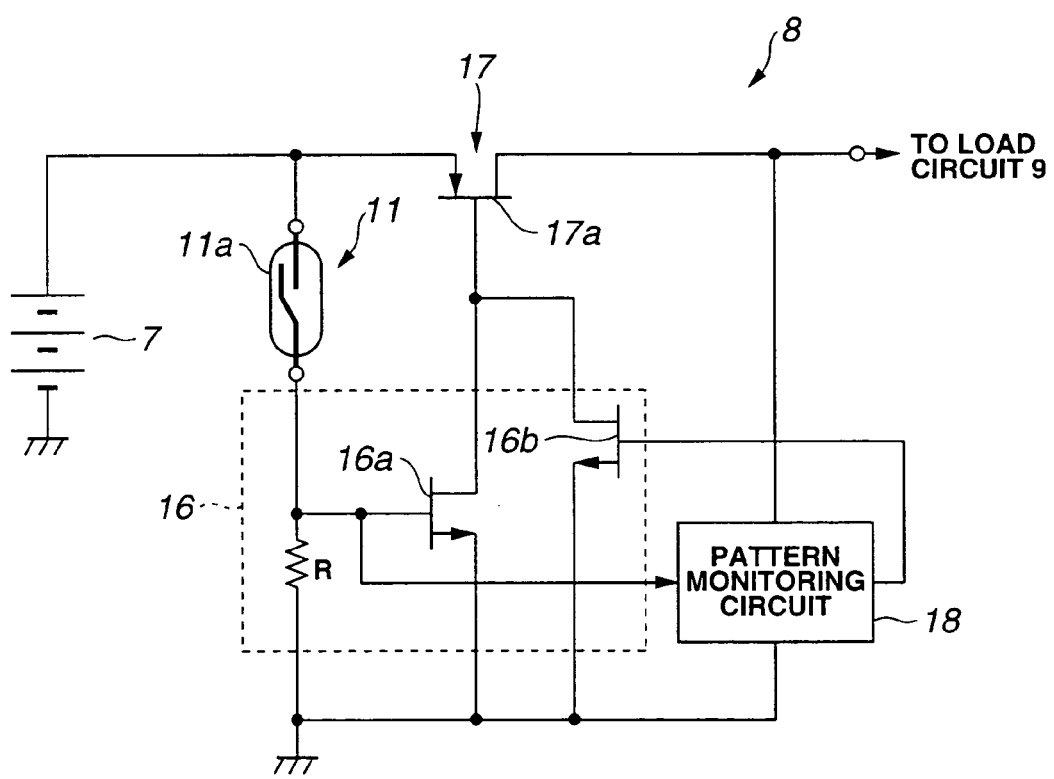
FIG. 3 is a circuit diagram illustrating a power switch circuit in the capsule type medical device in accordance with the first embodiment of the present invention.

FIG. 3 illustrates the structure of the power switch circuit 8. In the power switch circuit 8, the switch driver circuit 16 includes a resistor R, and two N-channel field effect transistors (hereinafter referred to as FETs) 16a and 16b. These elements form a NOR circuit, which on/off controls the semiconductor switch 17 including a P-channel FET 17a. When the magnetic sensor 11 (more specifically a reed switch 11a) is affected by the control of a physical quantity of magnetism, a binary voltage is caused at the node of the resistor R and the magnetic sensor 11. The pattern of the voltage is monitored by the pattern monitoring circuit 18.

The reed switch 11a is constructed of a glass tube in which magnetized reed contacts connected to lead wires are encapsulated. The reed switch 11a makes the connection in an on state in response to the application of a magnetic field to the center of the glass tube, and breaks the connection in an off state in response to the removal of the magnetic field. The reed switch 11a thus makes or breaks the connection in a non-contact manner. The response speed of the reed switch 11a is as high as about 500 Hz.

The structure of the power switch circuit 8 of FIG. 3 will now be specifically discussed. The positive electrode of the battery 7 is connected to the gate of FET 16a (first switch drive circuit as one of the two switch drive circuits) forming the switch driver circuit 16 via the magnetic sensor 11 (specifically, the reed switch 11a). The positive electrode of the battery 7 is also connected to a positive power input terminal of the load circuit 9 through the source and drain of FET 17a forming the semiconductor switch 17 and the output terminal of the power switch circuit 8.

The gate of FET 16a forming the first switch drive circuit is grounded through the resistor R, while being connected to the input terminal of the pattern monitoring circuit 18 that monitors the on and off pattern signal caused in response to the detection of magnetism of the reed switch 11a.

The drain of the FET 16a is connected to the gate of the FET 17a while being connected to the drain of FET 16b forming a second switch drive circuit. The sources of the two FETs 16a and 16b are connected to ground to which the negative electrode of the battery 7 is also connected.

The gate of FET 16b is connected to the output terminal of the pattern monitoring circuit 18. The pattern monitoring circuit 18 stores information of a predetermined pattern for switching from an off state to an on state in the same manner as the pattern signal generated by the pattern generator circuit 15 of the remote controller 3. The pattern monitoring circuit 18 determines whether the predetermined pattern matches a pattern of magnetism detected by the reed switch 11a. Depending on the determination result, the pattern monitoring circuit 18 causes the FET 16b to turn on, thereby turning on the semiconductor switch 17.

Alternatively, the gate of the FET 17a in the power switch circuit 8 may be connected to the positive electrode of the battery 7 via a high-resistance resistor so that the FET 17a is reliably non-conductive with FETs 16a and 16b turned off.

When a magnetic field is applied to the reed switch 11a in the capsule type medical device 2 in response to the operation of the remote controller 3, the reed switch 11a in the power switch circuit 8 is turned on in response to the detection of the magnetic field, thereby causing FET 16a to be turned on. With FET 16a turned on, the gate of the semiconductor switch 17 is driven low in level, and the semiconductor switch 17 is turned on. Power for operation is supplied to the pattern monitoring circuit 18, and the pattern monitoring circuit 18 starts performing a determination operation of the pattern signal.

Upon receiving power at first level 1 of the pattern signal, the pattern monitoring circuit 18 is supplied with power and is shifted into an operation state. The pattern monitoring circuit 18 starts a pattern monitoring operation with a slight delay from the transition of the pattern signal to a level 1. However, the pattern monitoring circuit 18 is not affected by the delay because the signal (at a level during level 0 period or level 1 period) is sampled at the same frequency and at a slightly delayed timing to perform the monitoring operation of determining whether the pattern matches the predetermined pattern.

The pattern monitoring circuit 18 determines whether the predetermined pattern matches the high and low gate level pattern of FET 16a in response to the on state and the off state respectively detected and undetected by the reed switch 11a.

If the pattern monitoring circuit 18 determines that the predetermined pattern matches an on pattern from an off state to an on state, the pattern monitoring circuit 18 outputs a high level signal from the output terminal thereof to the gate of FET 16b, thereby causing the semiconductor switch 17 to transition from off to on.

In accordance with the first embodiment, the remote controller 3 is used to cause the power switch circuit 8 to be transitioned from off to on. To transition the power switch circuit 8 from on to off, the external recording device 4 issues a command using wireless communication.

The operation unit 29 in the external recording device 4 is operated to transmit, from the wireless circuit 25 to the capsule type medical device 2, a control signal for causing the power switch circuit 8 to turn off. Upon receiving the control signal to turn off, the signal processor and controller circuit 23 in the capsule type medical device 2 transfers the control signal to the pattern monitoring circuit 18. The pattern monitoring circuit 18 turns FET 16b of the switch driver circuit 16 off, thereby turning off the semiconductor switch 17.

The operation of the power switch circuit 8 will now be discussed with reference to time charts illustrated in FIGS. 4A-4I.

FIGS. 4A-4I illustrate operation timings wherein, with power off, the remote controller 3 applies a magnetic field of a magnetism pattern for an on pattern to switch on the power of the capsule type medical device 2, and another magnetic field of another magnetism pattern.

As shown in FIG. 4A, on bit pattern 110100 . . . is set to switch on power. This on pattern information is also stored in the pattern monitoring circuit 18.

When the switch 14 in the remote controller 3 is operated, the pattern generator circuit 15 supplies the electromagnet 12 with pulse current in accordance with the on pattern. A magnetic field of a time series magnetism pattern is caused in response to the presence or absence of the pulse current.

The magnetism pattern has a frequency as high as about 400 Hz, and is thus within the response frequency of the reed switch 11a (commercially available reed switches have typically a response frequency of 500 Hz or so).

The magnetism pattern applied to the reed switch 11a is illustrated in FIG. 4B (with a high level in response to the presence of magnetism and a low level in response to the absence of magnetism). The reed switch 11a is turned on and off in response to the magnetism pattern.

In response to the on and off operation of the reed switch 11a, FET 16a is turned on and off, thereby changing the level at the output terminal thereof in response to the magnetism pattern as shown in FIG. 4C. As shown, the magnetism pattern is represented by crossing lines.

At the timing the reed switch 11a is turned on first, FET 16a is turned on. In response, the semiconductor switch 17 is turned on, thereby supplying power to the pattern monitoring circuit 18. The pattern monitoring circuit 18 then maintains the gate of FET 16b at a high level to keep the semiconductor switch 17 conductive for a duration of time Ta slightly longer than a short period of time required for pattern determination (see FIG. 4D). Regardless of the on and off operation of FET 16a, the pattern monitoring circuit 18 performs the pattern determination operation.

With the gate of FET 16b maintained at a high level, the semiconductor switch 17 is kept to be on, and the pattern monitoring circuit 18 monitors the pattern. The pattern monitoring circuit 18 determines whether the detected pattern matches the predetermined pattern. The pattern matching determination is completed prior to the end of the duration of time Ta.

If the detected pattern is determined to match the predetermined pattern, the pattern monitoring circuit 18 outputs a determination output signal of high level to the gate of FET 16b. The semiconductor switch 17 is kept to be on (see FIG. 4E). FIG. 4E shows timing "t" at which the pattern monitoring circuit 18 outputs the determination output signal determining that the detected pattern matches the predetermined pattern. The timing "It" appears prior to the end of time Ta.

If a magnetism pattern having a pattern different from the on pattern is applied as shown in FIG. 4F, the semiconductor switch 17 is turned on (see FIG. 4I) after FET 16a is first turned on. The pattern monitoring circuit 18 causes FET 16b to continuously turn on for the duration of time Ta to monitor the voltage pattern at the gate of FET 16a. FET 16a is turned on and off in response to the magnetism pattern. As in FIG. 4C, the magnetism pattern is represented by crossing lines in FIG. 4G.

Upon determining that the detected pattern fails to match the predetermined pattern, the pattern monitoring circuit 18 outputs a low-level determination signal to the gate of FET 16b. The timing of outputting the low-level determination signal is prior to the end of the duration of time Ta. At this timing, FET 16b is turned off, causing the semiconductor switch 17 to turn off.

In the case of the applied magnetism pattern shown in FIG. 4F, the timing of determination that the detected pattern fails to match the predetermined pattern comes prior to the timing of determination that the detected pattern matches the predetermined pattern. The timing of determination that the detected pattern fails to match the predetermined pattern varies depending on the magnetism pattern.

In accordance with the first embodiment of the present invention, the capsule type medical device 2 is switched on only when the magnetism pattern matching the predetermined magnetism pattern is applied. This arrangement reliably prevents the power of the capsule type medical device 2 from being erratically transitioned from off to on in response to different magnetism pattern. Furthermore, this arrangement prevents the capsule type medical device 2 from being erratically switched on in response to noise, thereby heightening reliability of the medical system.

Once the capsule type medical device 2 is switched on, the on state is maintained without the need for continuous application of the magnetism pattern.

The first embodiment of the present invention provides the advantages mentioned as below.

The power of the capsule type medical device 2 is switched on in response to the application of only the particular magnetism pattern generated by the dedicated remote controller 3. An erratic operation such as an inadvertent switch-on is prevented, and the reliability of the medical system is heightened. The ease of use is assured because the power of the capsule type medical device 2 is switched on by simply applying magnetism of the predetermined pattern temporarily.

Since it is sufficient if the magnetic sensor 11 detects the presence of magnetism, the switch-on operation is relatively free from sensitivity of detection. The medical system 1 thus enjoys the reliable detection feature of magnetism while providing robustness against disturbance.

In accordance with the first embodiment of the present invention, the power switch circuit 8 determines the presence or absence of magnetism having the particular pattern with almost no power supplied. In other words, when magnetism is not applied, the power switch circuit 8 consumes almost no power.

In the previous discussion, the particular magnetism pattern is used to shift the power of the capsule type medical device 2 from an off state to an on state. The present invention is applicable to the shifting of power from an on state to an off state.

The sensing characteristics of the magnetic sensor 11 is subject to the direction of magnetization thereof, therefore, the direction of an applied magnetic field.

This effect is controlled if a relative direction between the location of the magnetic sensor 11 and the electromagnet 12 of the remote controller 3 is restricted.

A second embodiment of the present invention will now be discussed with reference to FIG. 5.

Figure 5:
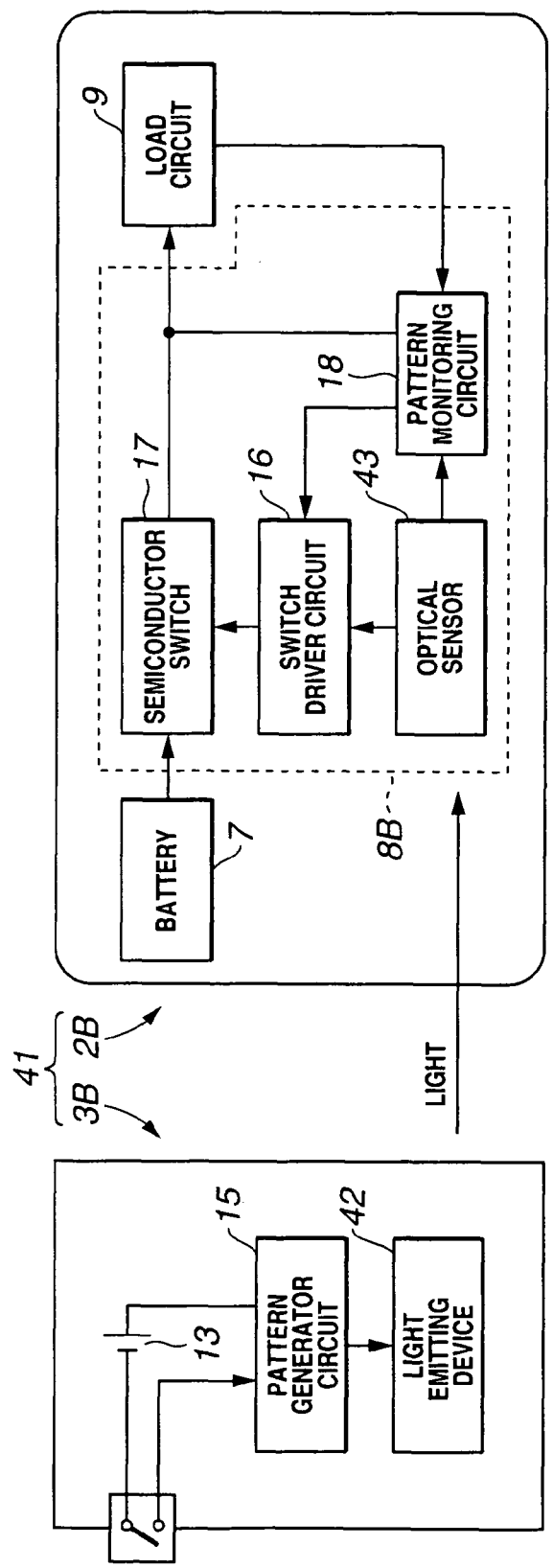
FIG. 5 is a block diagram illustrating the entire structure of the medical system in accordance with a second embodiment of the present invention.

FIG. 5 illustrates a medical system 41 of the second embodiment of the present invention. In the second embodiment, the medical system 41 includes light emitting means instead of the magnetism generating means and an optical sensor instead of the magnetic sensor 11 in the first embodiment.

The medical system 41 of FIG. 5 includes a capsule type medical device 2B and a remote controller 3B.

The remote controller 3B employs a light emitting device 42 instead of the electromagnet 12 of FIG. 1.

The capsule type medical device 2B includes the optical sensor 43, such as a photodiode, instead of the magnetic sensor 11. The optical sensor 43 forms a power switch circuit 8B.

The power switch circuit 8B includes a photodiode or a phototransistor instead of the reed switch 11a of FIG. 3.

In accordance with the second embodiment of the present invention, the power switch circuit 8B, including the photodiode or the phototransistor as the optical sensor 43, is integrated into a one-chip module, thereby permitting miniaturized, light-weight and low-cost design. The rest of the structure remains unchanged from the first embodiment of the present invention. The second embodiment of the present invention is almost identical in operation to the first embodiment of the present invention except that light is used instead of magnetism.

The second embodiment of the present invention permits miniaturized and low-cost design in addition to the advantages of the second embodiment of the present invention. In the case of magnetism, the detection of magnetism is subject to directionality depending on the direction of magnetization of the magnetic sensor. In contrast, the optical sensor 43 reliably switches on or off the power switch circuit 8B by irradiating the capsule type medical device 2 with light or by stopping light irradiation.

A third embodiment of the present invention will now be discussed with reference to FIGS. 7A-7I.

Figure 6:
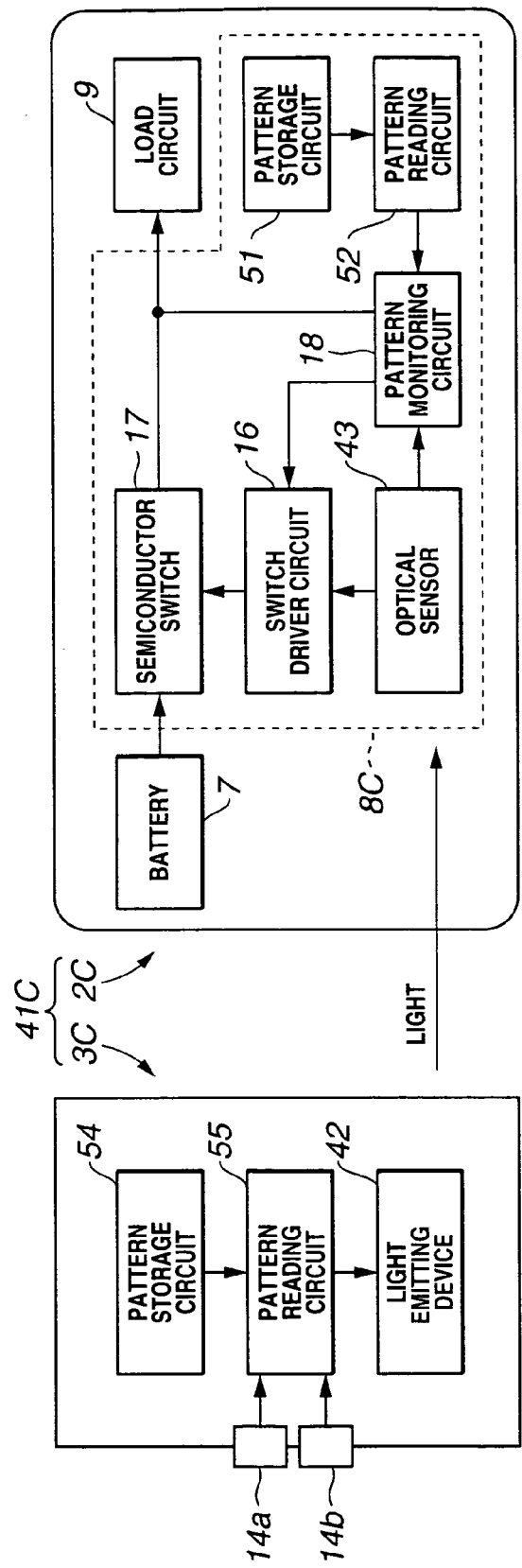
FIG. 6 is a block diagram illustrating the entire structure of the medical system in accordance with a third embodiment of the present invention.

FIG. 6 illustrates a medical system 41C of the third embodiment of the present invention. In the third embodiment of the present invention, a remote controller 3C is able to shift the power of a power switch circuit 8 from an off state to an on state, and from an on state to an off state in addition to the arrangement of the second embodiment of the present invention. The on pattern to switch on the power and the off pattern to switch off the power are set to be different to reliably switch on and off the power of the capsule type medical device 2.

As shown in FIG. 6, the medical system 41C includes a capsule type medical device 2C and a remote controller 3C.

The capsule type medical device 2C further includes a pattern storage circuit 51 and a pattern reading circuit 52 in addition to the power switch circuit 8B in the capsule type medical device 2B of FIG. 5.

As shown in FIG. 6, the power switch circuit 8C includes the following elements in addition to the power switch circuit 8B. More specifically, in addition to the power switch circuit 8B, the power switch circuit 8C further includes a pattern storage circuit 51 that stores information of an on pattern and an off pattern, and a pattern reading circuit 52 that reads the information of the on pattern and the off pattern from the pattern storage circuit 51 and outputs the information to the pattern monitoring circuit 18.

The remote controller 3C includes a pattern storage circuit 54 that stores information of an on pattern and an off pattern, a pattern reading circuit 55 that reads the information of the on pattern and the off pattern from the pattern storage circuit 54, and causes the light emitting device 42 to emit light in the form of pulse, an on switch 14a and an off switch 14b issuing read signals to the pattern reading circuit 55 to read the on pattern and the off pattern, respectively, and a battery (not shown) for feeding power to the pattern storage circuit 54, the pattern reading circuit 55, etc.

The pattern storage circuit 54 and the pattern reading circuit 55 in the remote controller 3C may be constructed of a microcomputer with a memory, and the pattern storage circuit 51, the pattern reading circuit 52, and the pattern monitoring circuit 18 in the capsule type medical device 2C may be constructed of a microcomputer with a memory.

The operation of the third embodiment of the present invention will now be discussed.

To put the capsule type medical device 2C into operation, the on switch 14a of the remote controller 3C is operated.

By operating the on switch 14a with the light emitting device 42 aligned with the optical sensor 43, the pattern reading circuit 55 is instructed to read the on pattern. The pattern reading circuit 55 reads the on pattern information from the pattern storage circuit 54, thereby causing the light emitting device 42 to emit light in response to the read information.

The on pattern may be the same one as indicated in FIG. 4A. The light emitting device 42 emits light at the level 1 and extinguishes at the level 0. A phototransistor as the optical sensor 43 is connected at the location of the reed switch 11a of FIG. 3, for example. When light is received, the phototransistor is turned on. In the same manner as the reed switch 11a, the semiconductor switch 17 is turned on, putting the pattern monitoring circuit 18 into operation.

As previously discussed, the semiconductor switch 17 is turned on for the pattern monitoring period (with FET 16b of FIG. 3 turned on).

The pattern monitoring circuit 18 reads the on pattern information from the pattern storage circuit 51 via the pattern reading circuit 52, and stores the on pattern information in a register of the pattern monitoring circuit 18, for example.

Since the optical sensor 43 (phototransistor) is turned on and off in response to a light emitting pattern of the light emitting device 42, the pattern monitoring circuit 18C determines whether the detected voltage pattern matches on pattern information stored in the register.

If the light pattern is substituted for the magnetism pattern of FIG. 4B, the operation of the capsule type medical device 2C also follows the pattern of FIG. 4B. When the on switch 14a in the remote controller 3C is operated, the pattern monitoring circuit 18C determines the detected voltage pattern matches the on pattern stored in the register, thereby turning the semiconductor switch 17 on.

Even if light of a pattern other than the on pattern is directed to the optical sensor 43, the semiconductor switch 17 is prevented from being turned on. If the capsule type medical device 2C is turned on, the illumination unit 21 emits light once or twice a second, and the image pickup unit 22 captures image in synchronization with the light emitting. The captured image signal is signal processed into image information by the signal processor and controller circuit 23. The image information is then wirelessly transmitted outwardly from the wireless circuit 24.

After the external recording device 4 verifies the operation of the capsule type medical device 2C, a patient may swallow the capsule type medical device 2C. Subsequent to the verification of the operation, the power of the capsule type medical device 2C may be turned off without being swallowed immediately.

To switch off the power of the capsule type medical device 2C, the off switch 14b of the remote controller 3C is turned on.

By operating the off switch 14b with the light emitting device 42 facing the optical sensor 43, a command to read an off pattern is issued to the pattern reading circuit 55. The pattern reading circuit 55 reads information of the off pattern from the pattern storage circuit 54, and causes the light emitting device 42 to emit light in accordance with the off pattern information.

For example, in response to the off pattern like the one shown in FIG. 7A, the light emitting device 42 emits light at level 1 and extinguishes at level 0 as shown in FIG. 7B.

If a phototransistor as the optical sensor 43 is connected instead of the reed switch 11a of FIG. 3, the phototransistor is turned on in response to received light, and turned off when the light emitting device 42 extinguishes. FET 16a is also turned on and off in response to the on and off operation of the phototransistor, as illustrated by crossing lines in FIG. 7C.

When FET 16a is turned on, the pattern monitoring circuit 18C starts a pattern signal determination process. The pattern monitoring circuit 18C keeps FET 16b conductive in an on state for a constant duration of time Ta (see FIG. 7D), and thus keeps the semiconductor switch 17 in an on state for the duration of time Ta.

The pattern monitoring circuit 18C reads the off pattern information from the pattern storage circuit 51 via the pattern reading circuit 52, and then stores the read off pattern information in a register or the like therein.

The optical sensor 43 (phototransistor) is turned on and off in response to the emission pattern of the light emitting device 42. The pattern monitoring circuit 18 determines whether the detected voltage pattern matches the off pattern information stored in the register or the like.

If the pattern monitoring circuit 18C determines that the detected voltage pattern matches the off pattern information stored in the register or the like, the semiconductor switch 17 is shifted from an on state to an off state as shown in FIG. 7E.

If the light emitting device 42 emits light in an emission pattern different from the off pattern (see FIG. 7F), FET 16a is turned on and off in accordance with that emission pattern (see FIG. 7G).

When FET 16a is turned on, the pattern monitoring circuit 18C starts a pattern signal determination process. The pattern monitoring circuit 18C keeps FET 16b conductive in an on state for a constant duration of time Ta (see FIG. 7H), and thus keeps the semiconductor switch 17 in an on state for the duration of time Ta.

If the pattern monitoring circuit 18C determines that the detected voltage pattern fails to match the off pattern, the pattern monitoring circuit 18C issues a non-coincidence determination signal to FET 16b to keep FET 16b and thus the semiconductor switch 17 conductive in an on state (see FIG. 7I).

In accordance with the third embodiment of the present invention, the capsule type medical device 2C is shifted from an off state to an on state or from an on state to an off state. The capsule type medical device 2C is reliably controlled for an off-to-on operation and an on-to-off operation.

By setting the on pattern different from the off pattern, the capsule type medical device 2C is more reliably switched on or off.

If a plurality of capsule type medical devices 2C are simultaneously used, erratic switching operations are easily prevented by modifying patterns stored in the pattern storage circuits 51 and 54. Depending on applications, the on pattern and the off pattern may be modified.

The pattern storage circuit 54 may be designed so that the stored pattern can be easily rewritten. For example, a point of contact for rewriting may be arranged. An external device (not shown) may be connected to the point of contact to rewrite the content of the pattern storage circuit 54 which may be EEPROM or flash memory as an electrically rewritable non-volatile memory.

The external recording device 4 may wirelessly transmit the pattern signal to the capsule type medical device 2C. The signal processor and controller circuit 23 forming the load circuit 9 may rewrite the pattern signal stored in the pattern storage circuit 51, which is constructed of an electrically rewritable non-volatile memory.

In the foregoing discussion, the pattern monitoring circuit 18C remains on while the semiconductor switch 17 is in an on state. Alternatively, the pattern monitoring circuit 18 may be shifted to an off state by the signal processor and controller circuit 23.

Information that the pattern monitoring circuit 18C has shifted the semiconductor switch 17 from an off state to an on state (or from an on state to an off state) may be stored in the pattern monitoring circuit 18C or the pattern storage circuit 51 containing an electrically rewritable non-volatile memory such as EEPROM. In response to the presence or absence of that information, the pattern reading circuit 52 may read the on pattern information or the off pattern information from the pattern storage circuit 51.

For example, when the pattern monitoring circuit 18C becomes operational with light input to the optical sensor 43, the pattern monitoring circuit 18C reads the on pattern if off-to-on shifting information is not stored, and determines whether the detected pattern matches the on pattern. If the off-to-on shifting information is stored, the pattern monitoring circuit 18C reads the off pattern and determines whether the detected pattern matches the off pattern.

The medical device examines the body by picking up images of internal organs in the preceding embodiments. The present invention is applicable to a medical device that performs medical treatment on an affected part or disperses drugs on an affected part.

In the foregoing discussion, the power of the capsule type medical device is switched on and off using any of light, magnetism, and radio waves. The switching control may be performed together with power feeding and position control of the capsule type medical device using any of light, magnetism, and radio waves.

A combination of the preceding embodiments in whole or in part falls within the scope of the present invention.

In this invention, it is apparent that working modes different in a wide range can be formed on this basis of this invention without departing from the spirit and scope of the invention. This invention is not restricted by any specific embodiment except being limited by the appended claims.

What is claimed is:

1. A medical system comprising:
    a capsule type medical device having a capsule configuration;
    an operation device, arranged external to the capsule type medical device, and including a binary signal generator for generating a binary signal having a particular pattern;
    a switch, arranged in the capsule type medical device, for switching on and off power of the capsule type medical device;
    a switch driver circuit for controlling the switch for a power on operation or a power off operation, the switch driver circuit being operative in response to the binary signal;
    a sensor, arranged in the capsule type medical device, which directly detects a binary signal applied from the outside and is used for the power on or off; and
    a pattern monitoring unit, arranged in the capsule type medical device, for monitoring whether or not the particular pattern is included in an output signal from the sensor;
    wherein in a state where the power of the capsule type medical device is off the switch is turned from an off state to an on state when the pattern monitoring unit detects the binary signal from an output signal of the sensor, the switch is turned to the on state long enough for the pattern monitoring unit to determine if the particular pattern is included in the binary signal, the switch is kept in the on state if the pattern monitoring unit determines that the particular pattern is included in the binary signal, and the switch is turned to the off state if the pattern monitoring unit determines that the particular pattern is not included in the binary signal.

2. A medical system according to claim 1, wherein the operation device generates two different patterns as the binary signal having the particular pattern.

3. A medical system according to claim 1, further comprising a storage unit for storing information of the particular pattern, and a reading unit for reading the information of the particular pattern from the storage unit.

4. A medical system according to claim 1, wherein the operation device comprises:
    a storage unit for storing an on pattern and an off pattern as information of the particular pattern, and
    a reading unit for reading one of the on pattern and the off pattern in response to the operation of the operation device.

5. A medical system according to claim 1, wherein the capsule type medical device comprises:
    a storage unit for storing an on pattern and an off pattern as information of the particular pattern, and
    a reading unit for reading at least one of the on pattern and the off pattern.

6. A medical system comprising:
    a capsule type medical device having a capsule configuration;
    an operation device, arranged external to the capsule type medical device, and including a binary signal generator for generating a binary signal having a particular pattern;
    a semiconductor switch, arranged in the capsule type medical device, for at least switching on from off power of the capsule type medical device;
    a switch driver circuit, arranged in the capsule type medical device, for controlling the semiconductor switch for a power on operation or a power off operation, the switch driver circuit being operative in response to the binary signal;

a sensor, arranged in the capsule type medical device, which directly detects a binary signal applied from the outside and is used for the power on or off; and a pattern monitoring unit, arranged in the capsule type medical device, for monitoring whether or not the particular pattern is included in an output signal from the sensor;

wherein in a state where the power of the capsule type medical device is off the semiconductor switch is turned from an off state to an on state when the pattern monitoring unit detects the binary signal from an output signal of the sensor, the semiconductor switch is turned to the on state long enough for the pattern monitoring unit to determine if the particular pattern is included in the binary signal, the semiconductor switch is kept in the on state if the pattern monitoring unit determines that the particular pattern is included in the binary signal, and the semiconductor switch is turned to the off state if the pattern monitoring unit determines that the particular pattern is not included in the binary signal.

7. A medical system according to claim 6, wherein the operation device selectively generates a first pattern and a second pattern different from each other as the binary signal having the particular pattern.

8. A medical system according to claim 6, further comprising a storage unit for storing information of the particular pattern, and a reading unit for reading the information of the particular pattern from the storage unit.

9. A medical system according to claim 6, wherein the operation device comprises:
a storage unit for storing an on pattern and an off pattern as information of the particular pattern, and
a reading unit for reading one of the on pattern and the off pattern in response to the operation of the operation device.

10. A medical system according to claim 6, wherein the capsule type medical device comprises:
a storage unit for storing an on pattern and an off pattern as information of the particular pattern,
a reading unit for reading at least one of the on pattern and the off pattern.

11. A medical system according to claim 6, wherein the generator is light emitting unit for generating a binary signal having an optical particular pattern, and wherein the receiver is a light receiver sensitive to light.

12. A medical system according to claim 11, wherein the light receiver comprises a light receiver device, and is provided on the same semiconductor as the semiconductor switch and the switch driver circuit.

13. A medical system comprising:
a capsule type medical device having a capsule configuration;
an operation device, arranged external to the capsule type medical device, and including a binary signal generator for selectively generating a binary signal having two different patterns;
a semiconductor switch, arranged in the capsule type medical device, for switching on from off and off from on power of the capsule type medical device;
a switch driver circuit, arranged in the capsule type medical device, for controlling the semiconductor switch for a power on operation or a power off operation, the switch driver circuit being operative in response to the binary signal;

a sensor, arranged in the capsule type medical device, which directly detects a binary signal applied from the outside and is used for the power on or off; and a pattern monitoring unit, arranged in the capsule type medical device, for monitoring an output signal of the sensor and for driving the switch driver circuit that controls the semiconductor switch for the power on operation at the moment the pattern monitoring unit detects an on pattern that is one of the two particular patterns in the output of the sensor during the monitoring period, and for driving the switch driver circuit that controls the semiconductor switch for the power off operation at the moment the pattern monitoring unit detects an off pattern that is the other of the two particular patterns in the output of the sensor during the monitoring period;

wherein in a state where the power of the capsule type medical device is off the semiconductor switch is turned from an off state to an on state when the pattern monitoring unit detects the binary signal from an output signal of the sensor, the semiconductor switch is turned to the on state long enough for the pattern monitoring unit to determine if the particular pattern is included in the binary signal, the semiconductor switch is kept in the on state if the pattern monitoring unit determines that the particular pattern is included in the binary signal, and the semiconductor switch is turned to the off state if the pattern monitoring unit determines that the particular pattern is not included in the binary signal.

14. A medical system comprising:
a capsule type medical device having a capsule configuration;
a sensor, arranged in the capsule type medical device, for directly detecting a binary signal that is applied by light or a magnetic field coming in from outside the capsule type medical device for the power on operation or the power off operation;
a pattern monitoring unit for determining whether a time-series binary signal on the basis of detecting or undetecting by the sensor matches a particular pattern; and
a switch for switching the power of the capsule type medical device between an on state and an off state at the moment the pattern monitoring unit determines that the binary signal matches the particular pattern;
a switch driver circuit for controlling the switch for a power on operation or a power off operation, the switch driver circuit being operative in response to the binary signal;
wherein in a state where the power of the capsule type medical device is off the switch is turned from an off state to an on state when the pattern monitoring unit detects the binary signal from an output signal of the sensor, the switch is turned to the on state long enough for the pattern monitoring unit to determine if the particular pattern is included in the binary signal, the switch is kept in the on state if the pattern monitoring unit determines that the particular pattern is included in the binary signal, and the switch is turned to the off state if the pattern monitoring unit determines that the particular pattern is not included in the binary signal.

15. A medical system according to claim 14, further comprising an operation device, arranged external to the capsule type medical device, for generating the time series binary signal having the particular pattern which is used by the pattern monitoring unit to perform the determination.

* * * * *